(12) United States Patent
Boit et al.

(10) Patent No.: US 9,234,049 B2
(45) Date of Patent: Jan. 12, 2016

(54) COMPRESSIBLE, HIGHLY VISCOUS POLYSACCHARIDE AND POLYOL POWDER

(75) Inventors: Baptiste Boit, Bethune (FR); Fabrice Buquet, Renescure (FR); Gregory Le Bihan, Annezin (FR); Philippe Lefevre, Haverskerque (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 13/880,506

(22) PCT Filed: Nov. 2, 2011

(86) PCT No.: PCT/FR2011/052559
§ 371 (c)(1),
(2), (4) Date: Apr. 19, 2013

(87) PCT Pub. No.: WO2012/059689
PCT Pub. Date: May 10, 2012

(65) Prior Publication Data
US 2013/0289055 A1    Oct. 31, 2013

(30) Foreign Application Priority Data
Nov. 2, 2010    (FR) ..................................... 10 59024

(51) Int. Cl.
| | | |
|---|---|---|
| C08B 31/12 | (2006.01) |
| A61K 47/26 | (2006.01) |
| A61K 47/36 | (2006.01) |
| C08L 3/02 | (2006.01) |
| C08L 5/00 | (2006.01) |
| A61K 47/38 | (2006.01) |
| C08B 11/08 | (2006.01) |
| C08B 37/00 | (2006.01) |

(52) U.S. Cl.
CPC .................. *C08B 31/12* (2013.01); *A61K 47/26* (2013.01); *A61K 47/36* (2013.01); *A61K 47/38* (2013.01); *C08B 11/08* (2013.01); *C08B 37/00* (2013.01); *C08B 37/0084* (2013.01); *C08L 3/02* (2013.01); *C08L 5/00* (2013.01); *Y10T 428/2982* (2015.01)

(58) Field of Classification Search
CPC ....................................................... C08B 31/12
See application file for complete search history.

(56) References Cited

U.S. PATENT DOCUMENTS

| | | | |
|---|---|---|---|
| 4,156,020 A | 5/1979 | Bohrmann et al. |
| 6,770,368 B2 | 8/2004 | Luhn |
| 2001/0055648 A1 | 12/2001 | Lee et al. |

FOREIGN PATENT DOCUMENTS

| | | |
|---|---|---|
| EP | 1 175 899 A1 | 1/2002 |
| FR | 08 54584 A | 4/1940 |
| FR | 2 826 549 A1 | 1/2003 |
| WO | 99/52512 A1 | 10/1999 |
| WO | 03/061647 A1 | 7/2003 |
| WO | 2004/041254 A1 | 5/2004 |
| WO | 2010/017358 A1 | 2/2010 |
| WO | WO 2010017358 A1 * | 2/2010 |
| WO | WO2010017358 A1 * | 2/2010 |

OTHER PUBLICATIONS

World English Dictionary. "Mannitol." © 2009. Available from: < http://dictionary.reference.com/browse/mannite >.*
International Search Report, dated Feb. 3, 2012, from corresponding PCT application.

* cited by examiner

Primary Examiner — Andrew D Kosar
Assistant Examiner — John S Kenyon
(74) Attorney, Agent, or Firm — Young & Thompson

(57) ABSTRACT

A powder of cold-soluble polysaccharide and polyol, which is highly viscous in water and suitable for direct compression, and a method for preparing the powder and uses thereof are described, the powder being notably intended for preparing solid forms with controlled release of an active principle.

17 Claims, 2 Drawing Sheets

Figure 1 – Theophylline dissolution profile

COMPRESSIBLE, HIGHLY VISCOUS POLYSACCHARIDE AND POLYOL POWDER

FIELD OF THE INVENTION

The invention relates to a cold-soluble-polysaccharide and polyol powder, the said powder being highly viscous in water and being suitable for direct compression. The invention also relates to a method for preparing said powder and to the uses thereof, the powder being in particular intended for preparing solid forms with controlled release of an active ingredient.

PRIOR ART

In the field of pharmaceutical and nutraceutical excipients, controlled-release matrix compositions, also known as controlled-release matrices, allow the administration of an effective dose of active ingredient at a constant and uniform plasma concentration over a long period of time. Controlled-release matrices are thus particularly advantageous for the patients since they make it possible to optimize the treatment while at the same decreasing the frequency with which tablets have to be taken and reducing the plasma peaks of active ingredient and, consequently, the potential adverse effects.

Over the past few years, controlled-release hydrophilic matrices have been widely developed. In matrix compositions of this type, the active ingredient is dispersed in a solid hydrophilic matrix. The release of the active ingredient out of the matrix is carried out by virtue of the contact of biological fluids with said matrix. More specifically, biological fluids migrate through the matrix, causing swelling of said matrix, and solubilizing the active ingredients which then diffuse through the hydrated matrix network. The gradual diffusion of the active ingredients through the matrix modulates the release flow.

Among the oral forms usable for the controlled release of active ingredients, tablets which can be obtained by direct compression are of major interest for pharmaceutical industries since they are simple to produce from a pharmaceutical technical point of view and their release properties are easily modulatable.

Many polymers which are soluble in water at room temperature (cold-soluble polymers) have been proposed for controlled-release hydrophilic matrices. Among the polymers most widely used in these formulations, synthetic polymers and copolymers of acrylic and methacrylic acids, and cold-soluble polysaccharides such as galactomannans, originating in particular from vegetable gums, cellulose derivatives such as hydroxypropylmethylcellulose (HPMC) and pregelatinized starches, are widely represented.

These polysaccharides have in common the fact that they are highly viscous in water. This high viscosity complicates the obtaining thereof in powder form. Furthermore, their very large molecular size limits their crystallization and results in powders which are predominantly amorphous, elastic and generally fibrous in appearance, which makes it difficult to mill. Obtaining a powder of polysaccharides with precise physical properties is therefore complex. Consequently, these polysaccharide powders flow with difficulty and are not very compressible, making them difficult to use for producing tablets.

By way of example of the technical problems encountered during the industrial use of cold-soluble polysaccharides, mention may be made of the particular case of pregelatinized starch. This polysaccharide is one of the most attractive biopolymers as an excipient for controlled-release matrices because it can be produced on a large-scale with high purity and at a low economic cost. Starch is, moreover, biocompatible, biodegradable and nontoxic and can therefore even be used for nutraceutical purposes. It also has a high swelling capacity in water. In addition, starch has the advantage of being able to be used as a bulking agent, a binder or a diluent. However, its high viscosity and its small particle size give it very poor flow properties. The high elasticity of starch gives it a low compressibility which does not enable the production of tablets by direct compression. Thus, pregelatinized starch is regularly used in small amounts.

In order to remedy this situation, it is known practice by specialists in the field to use a pregelatinized starch of which a step of its method of production consists of precipitation in an organic solvent. The resulting pregelatinized starch not only has the known advantages of pregelatinized starch, namely in particular its controlled-release hydrophilic matrix properties, but is also readily compressible and allows the production of tablets by direct compression.

Unfortunately, these techniques call for the use of large amounts of organic solvents, thereby making their industrialization particularly difficult to implement.

Furthermore, it is essential to collect the organic solvents in order to prevent them from being dispersed in the atmosphere.

Finally, traces of toxic solvent can remain in the final product.

In other words, the preparation of these compositions results in a particularly high environmental and economic cost owing in particular to the need to use large amounts of organic solvents and to the numerous technical constraints to be overcome.

In order to improve the rheological properties of excipients, and in particular of cold-soluble polysaccharides, it is known to those skilled in the art to combine them with other excipients and/or to texture them using particular techniques such as granulation, simple or multi-stage spray drying, encapsulation, agglomeration, etc.

Among the excipients most commonly encountered for the preparation of tablets, mention may in particular be made of lactose, saccharose, glucose, trehalose, mannitol, sorbitol, erythritol, maltitol and isomalt.

Mannitol, owing to the low hygroscopiscity of its crystalline form, is capable of constituting an excellent excipient. Moreover, mannitol is, among the soluble excipients, the one which gives the greatest stability to medicinal solid forms, by virtue of its very high chemical inertia with respect to active ingredients.

The applicant has previously proposed, in its patent application FR 08.54584, granules of mannitol and of granular starch which can be obtained by spray drying and which are characterized in that they make it possible to prepare, by direct compression, orodispersible tablets which have in particular a notable hardness.

Unfortunately, in the particular field of controlled-release matrices, it is a question of texturing not a granular starch, which is insoluble in water, but a cold-soluble polysaccharide which is highly viscous in an aqueous medium.

As it happens, it is known to those skilled in the art (as indicated in particular in patent U.S. Pat. No. 4,156,020) that cold-soluble polysaccharides or compositions containing soluble polysaccharides, in particular pregelatinized starch, cannot be textured by spray drying when the starch is thus present in the cold, swollen and viscous state. Indeed, dehydrating cold-soluble products, even using vapor jets, results in the formation of viscous, nontexturable lumps.

It has been proposed, in patent application WO 2010/017358 to spray dry a cold-soluble polysaccharide (in particular guar gum or inulin) by preparing a suspension/solution of said polysaccharide with mannitol. In the words of the proprietor of application WO 2010/017358, the addition of mannitol to the suspension/solution of polysaccharide enables a drop in the viscosity of said solution, which can then be spray dried. However, this technique has a certain number of disadvantages. In particular, only a suspension/solution containing low concentrations of products can be spray dried (suspension/solution at 0.25% to 1.0% by weight of polysaccharide, polysaccharide/mannitol ratio of 1/05 to 1/10), and this results in a strong hydration of the polysaccharide before texturing and difficulty in drying said polysaccharide. Furthermore, the resulting final product exhibits a spherical shape, disappearance of the polysaccharide in the particulate state, and a small particle size (between 1 and 20 µm) unsuitable for direct compression, this technique imposing the lowest possible content of particles of less than 40 µm, ideally less than 5% (weight/weight) of the total powder. Moreover, the final product by itself does not allow the production of tablets capable of being obtained by direct compression. It is necessary to add large amounts of microcrystalline cellulose to the composition in order to make it compressible.

From all the aforementioned, it emerges that there is an unsatisfied need to have a product which, on its own, has the characteristics suitable both for the industrial production of controlled-release hydrophilic matrices and for that of tablets capable of being obtained by direct compression, these characteristics generally being incompatible.

The applicant has therefore, to its credit, gone against a technical preconception which has endured for many years, and has thus succeeded in reconciling the above mentioned rheological characteristics.

Thus, a first objective of the present invention is to provide a product which has, by itself, the characteristic suitable both for the industrial production of controlled-release hydrophilic matrices and for that of tablets by direct compression.

A second objective of the present invention is to provide controlled-release matrices of which the composition does not significantly vary from one batch to the other and remains stable over the time.

Another objective of the invention is to provide biocompatible, biodegradable and nontoxic controlled-release matrices which can be easily prepared.

Another objective of the present invention is to provide controlled-release matrices of which the production cost, both in economic and in environmental terms, is low.

Yet another objective of the present invention consists of the production of pulverulent compositions which have very good flow and are therefore suitable for the high-rate production of solid forms on tablet presses.

Yet another objective of the present invention consists of the production of tablets which exhibit a high composition homogeneity, since the powder according to the invention does not induce any demixing problem conventionally found in the solid form industry.

Finally, another objective of the present invention is to provide a method for preparing a powder suitable for any cold-soluble polysaccharide, in particular for any polysaccharide which exhibits a high viscosity in water at room temperature.

SUMMARY OF THE INVENTION

A subject of the invention is a powder of cold-soluble-polysaccharide and of polyol, the polysaccharide and the polyol exhibiting physical bonds between them, the polysaccharide being in particulate form and the polyol being predominantly in crystalline form.

The invention also relates to a method for preparing the powder according to the invention, characterized in that it comprises a texturing step comprising:
  spraying a polyol syrup onto a cold-soluble polysaccharide in particulate form, and simultaneously
  drying said polyol syrup.

Finally, a subject of the invention is solid forms comprising the powder according to the invention and the use thereof for controlled release of an active ingredient.

DETAILED DESCRIPTION

Figure 1:
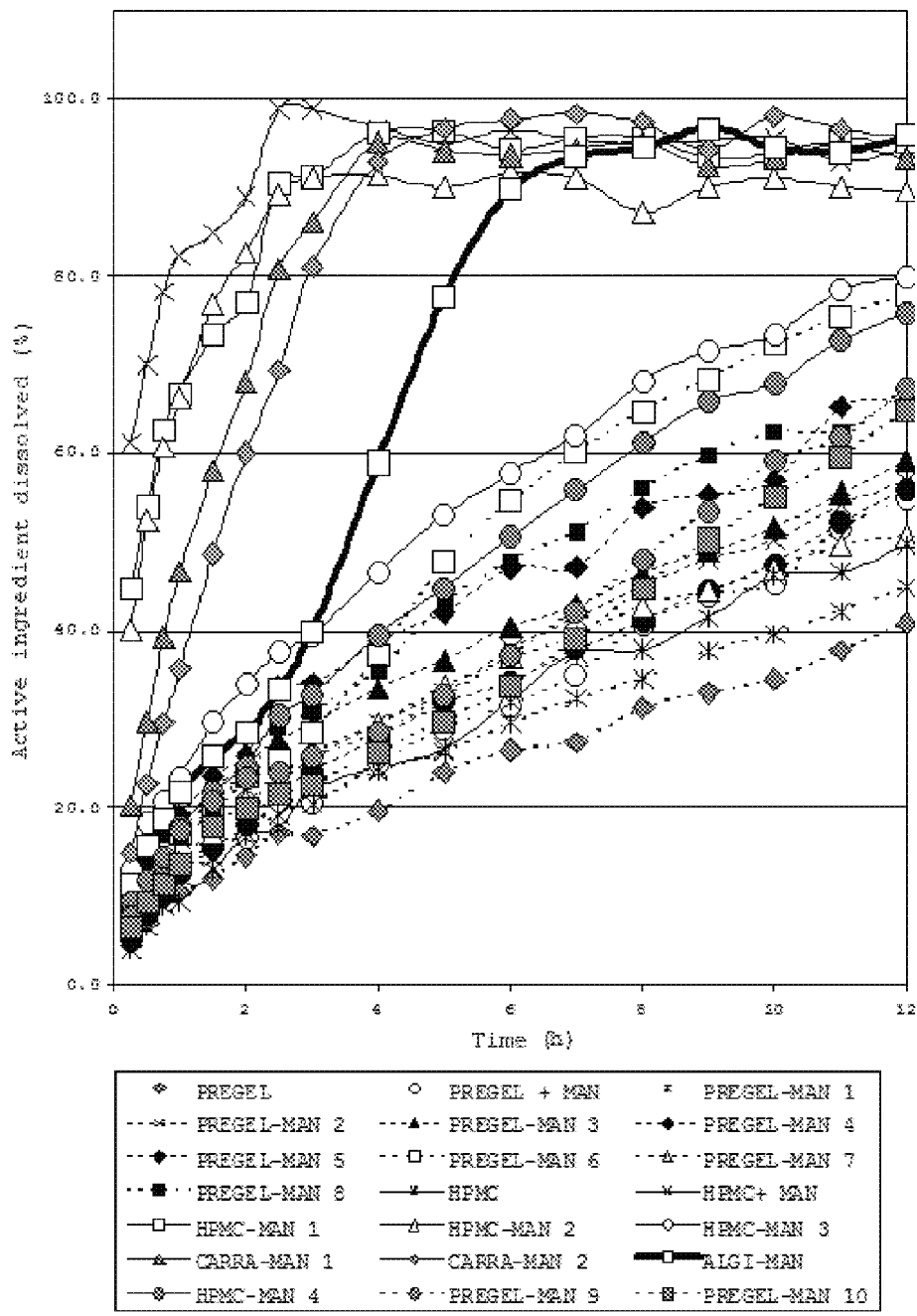
FIG. 1 shows the curves of controlled release of an active ingredient (theophylline) with various powders, according to the invention and outside the invention.

The present invention first relates to a powder of cold-soluble-polysaccharide and of polyol. According to the invention, the polysaccharide, in particulate form, and the polyol, predominantly in crystalline form, of the powder have physical bonds between them.

In the present invention, the term "cold-soluble polysaccharide" is intended to mean any polymer, consisting of several monosaccharides linked to one another via O-glycosidic bonds, at least 90% by weight of said polysaccharide of which is soluble in water at 20° C.±2° C. Such solubility at 20° C. makes it possible to be sure of the solubility of the polysaccharide at the temperature of the human body, of about 37° C. By way of examples, mention may be made, among cold-soluble polysaccharides, of:
  chemically modified cellulose derivatives, such as hydroxyethylcellulose (HEC), hydroxypropylcellulose (HPC) or hydroxypropylmethylcellulose (HPMC),
  native or modified hemicelluloses,
  pregelatinized starches, whether they are native or chemically modified,
  polysaccharides derived from plants, such as pectins, guar gum, konjac gum, sterculia gum, locust bean gum or gum arabic,
  polysaccharides derived from algae, such as agar-agar, carrageenans, alginates and salts thereof,
  polysaccharides derived from microorganisms such as xanthan gum or pullulan,
  and also the derivatives of the abovementioned polysaccharides, and mixtures thereof.

Thus, the present invention also relates to a powder of polysaccharide and of polyol, wherein the polysaccharide is selected from the group consisting of pregelatinized starches, chemically modified cellulose derivatives, hemicelluloses, polysaccharides derived from plants, polysaccharides derived from algae or from microorganisms, the derivatives of these polysaccharides, and mixtures thereof.

Preferably, a subject of the present invention is a powder of polysaccharide and of polyol, wherein the polysaccharide is selected from the group consisting of hydroxyethylcellulose (HEC), hydroxypropylcellulose (HPC) or hydroxypropylmethylcellulose (HPMC), native or chemically modified pregelatinized starches, agar-agar, carrageenans, alginates and salts thereof, xanthan gum, pullulan, derivatives of these polysaccharides, and mixtures thereof.

In the present invention, the term "polysaccharide in particulate form" is intended to mean a polysaccharide in the form of a powder of which the particles forming the powder have a volume mean diameter D4,3 of between 10 and 200 μm, preferably between 20 and 150 μm, and even more preferentially between 50 and 100 μm. The polysaccharide particles also have a high viscosity in water, in particular a viscosity greater than 200 mPa·s$^{-1}$ when they are in solution in a proportion of from 1% to 5% by weight of dry matter (DM).

In the present invention, the term "polyol" is intended to mean a compound selected from the group consisting of mannitol, sorbitol, isomalt, and mixtures thereof.

In the present invention, the term "physical bond" is intended to mean the agglomeration of polysaccharide in dry and particulate form with a polyol, said agglomeration resulting from the drying (or dehydration) of a syrup of said polyol sprayed onto or around the polysaccharide. This drying thus results in an adhesion or physical bond between the polysaccharide and the polyol which goes from a solubilized state to a predominantly crystalline or microcrystalline state. The term "predominantly crystalline" or "predominantly in crystalline form" is intended to mean here the fact that the value of the enthalpy of fusion of the polyol of the powder ($\Delta H_{powder}$), measured by DSC (Differential Scanning Calorimetry) and weighted with respect to the weight of polyol present in the powder according to the invention (% polyol by weight), is at least greater than 70% of the value of the enthalpy of fusion of the crystalline polyol alone ($\Delta H_{polyol\ alone}$) also measured by DSC, i.e.:

$$\Delta H_{powder} > 0.7 \times ((\Delta H_{polyol\ alone}) \times (\% \text{ polyol by weight})/100)$$

Thus, the powder of the present invention differs via its presentation form and, consequently, via its technical characteristics, from a simple physical mixture in which the polysaccharide and the polyol are present in the form of independent, i.e. nonbound, entities. The powder of the present invention also differs, via its presentation form and its technical characteristics, from a co-agglomerate resulting from the drying of a suspension/solution of polysaccharide and of polyol in which the polysaccharide and the polyol have covalent chemical bonds between them, for example hydrogen bonds.

The powder according to the invention can be obtained by virtue of a method comprising a texturing step comprising spraying a polyol syrup onto a cold-soluble polysaccharide in particulate form and simultaneously drying said polyol syrup.

During this texturing step, the polysaccharide in particulate form can be introduced in continuous mode or batchwise mode.

In the present invention, the term "spraying" is intended to mean the division of a polyol syrup into fine droplets by means of a nozzle or by means of a turbine. In order to be sprayed, the polyol syrup is maintained at a temperature between 40 and 120° C., such a temperature thus making it possible to keep the polyol in the dissolved state. The polyol syrup also has a dry matter (DM) content of between 15% and 95% by weight.

The texturing step must allow sufficiently rapid drying to prevent hydration of the polysaccharide in particulate form and to also prevent the polyol syrup and/or the polysaccharide from setting solid.

In the present invention, the term "drying" is intended to mean the dehydration of the sprayed polyol syrup by any means whatsoever. In particular, the drying can be carried out by convection, by conduction or by waves, in particular by microwaves or infrared waves. According to a preferred mode of the present invention, the drying is carried out with air having a temperature of between 40 and 300° C.

Preferably, the texturing step can be carried out in a spray-drying tower or a fluidized air bed granulator.

According to one particular mode of the method of the present invention, the texturing step is carried out in a spray-drying tower, for example a spray-drying tower of MSD (i.e. Multi Stage Dryer) type fitted with a high-pressure spray-drying nozzle.

The spray-drying chamber of the spray-drying tower comprises a spraying zone (at the top of the chamber) fitted with a principal drying air (upstream air) inlet. The spray-drying chamber also comprises, at the bottom of the chamber, a static fluidized bed with a specific air (static bed air) inlet. The temperature of the inlet airs is set in the following way:

upstream air at the top of the tower: temperature between 120° C. and 240° C.,
static bed air: temperature between 40° C. and 120° C.

Preferably, the spray-drying chamber comprises two powder injection points, one located at the top of the chamber and one located at the bottom of the chamber for introducing the polysaccharide.

The spray-drying tower is also advantageously equipped with a cycloning system which makes it possible to recover the fine particles (for example, advantageously, the particles with a particle size of less than 100 μm) carried by the outlet air stream of the spray-drying chamber. Thus, according to one particular mode of the method according to the invention, the texturing step also comprises the recycling of a powder fraction. The term "powder fraction" is intended to mean here the recycling of the fine particles of powder and, optionally, a part of the powder according to the invention, which is milled or unmilled.

In the case of the use of an MSD-type spray-drying tower, the recycling can be carried out by injection of the powder fraction at the top or at the bottom of the spray-drying chamber.

According to one particular mode of the method according to the invention, the powder is subjected to an optional step of additional drying, after the texturing step. The additional drying step can be carried out, for example, in a fluidized air bed.

Following the texturing step or after the optional additional drying step, the powder is subjected to a cooling step. According to one preferred mode of the method of the invention, the cooling to a temperature of less than 30° C. is carried out on a fluidized bed of which the air temperature is between 15 and 25° C.

The optional additional drying step and the cooling step can be combined in a vibrated fluidized air bed composed of two zones (one used for the drying step and the other used for the cooling step).

According to one particular mode of the method according to the invention, the powder is subjected to an optional sieving step. Said sieving step is carried out with, in particular, one or two cloths or sieves. Thus, the powder fractions that are too fine and/or too coarse can be eliminated. Moreover, the sieved and unwanted powder fractions can be recycled (directly or after milling) for the texturing step.

The method according to the invention thus makes it possible to obtain a powder of cold-soluble-polysaccharide and of polyol. The polysaccharide of said powder, in particulate form, and the polyol, predominantly in crystalline form, are physically linked to one another. The polyol/polysaccharide ratio of the powder according to the invention is between 95/5 and 30/70, preferably between 90/10 and 40/60, and even more preferentially between 85/15 and 50/50.

Figure 5:

The particles of the powder according to the invention have an irregular, substantially nonspherical shape (FIGS. 2 to 5). Within or at the surface of said particles according to the invention, the polysaccharide in the particulate state is still clearly visible, as is the polyol predominantly present in the crystalline or microcrystalline state (FIG. 5 in particular). The powder according to the invention can also have a particle size D4,3 of between 50 and 500 µm, preferably between 80 and 300 µm, and even more preferentially between 100 and 250 µm.

In the present invention, the particle size of the pulverulent products is determined on an LS 13-320 LASER diffraction particle size analyzer from the company Beckman-Coulter, equipped with its powder dispersion module (dry process), according to the technical manual and the specifications of the constructor.

The operating conditions of subhopper screw speed and of intensity of vibration of the dispersion chute are determined such that the optical concentration is between 4% and 12%, ideally 8%.

The measurement range of the LS 13-320 LASER diffraction particle size analyzer is from 0.04 µm to 2000 µm. The results are calculated as percentage by volume and expressed in µm.

The particle size distribution curve makes it possible to determine the value of the volume mean diameter (arithmetic mean) D4,3.

Preferably, the powder according to the invention has a viscosity in water, evaluated according to a test A described hereinafter, of between 100 mPa·s$^{-1}$ and 10000 Pa·s$^{-1}$, preferably between 200 mPa·s$^{-1}$ and 5000 Pa·s$^{-1}$, and even more preferentially between 400 mPa·s$^{-1}$ and 1000 Pa·s$^{-1}$.

The test A consists in:
preparing a suspension/solution of the sample to be tested by incorporating 10.0 g of sample into 90.0 g of distilled water at 20±2° C.;
leaving the suspension/solution to hydrate for 1 h and homogenizing it by stirring;
measuring the viscosity at 20° C.±2° C. using the Physica MCR301 rheometer equipped with a measuring geometry of cone-plate type with a diameter of 5 cm and a 1° of angle, sold by the company Anton Paar, according to the instructions and the recommendations of the constructor (the shear gradient fixed at 5 s$^{-1}$ is given by the angular speed in rad·s$^{-1}$).

Preferably, the powder according to the invention has a flow time, determined according to a test B, of between 3 and 15 seconds, preferably between 4 and 12 seconds and even more preferentially between 5 and 10 seconds.

Figure 2:
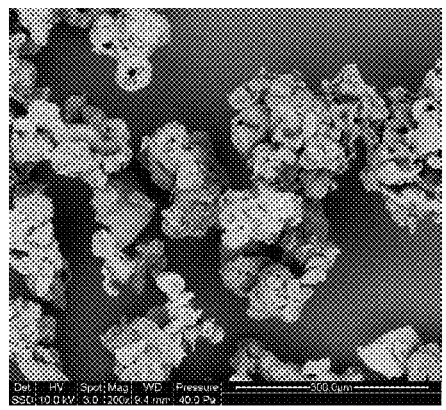
FIGS. 2 to 5 represent photographs of observations, made with a scanning microscope, of four powders according to the invention, at various magnifications.
Figure 3:
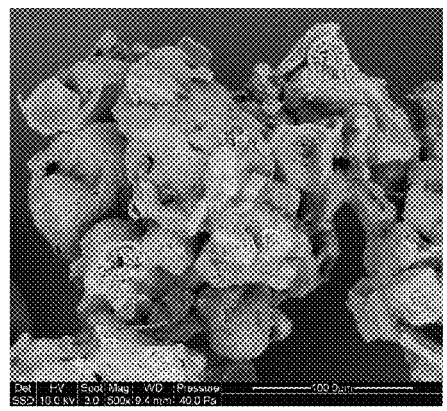
Figure 4:
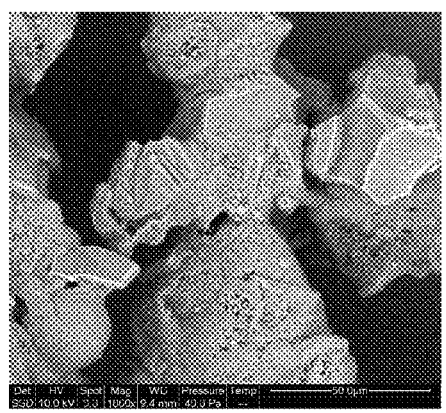

The test B consists in determining the time necessary for the flow of 100.0 g of powder according to the method of measurement recommended by the European Pharmacopea (EP 5.0 volume 1, 01/2005:20916, section 2.9.1.6; equipment according to FIG. 2.9.16.-2).

The powder according to the invention is, moreover, advantageously characterized by its bulk density and its tapped density, determined according to test C corresponding in particular to the method of measurement recommended by the European Pharmacopea (EP 5.1 volume 1, 01/2005: 20915 section 2-9-15; equipment according to FIG. 2-9-15-1) and also by its compressibility.

Briefly, the test C consists in introducing 100 g of powder into a 250 ml graduated cylinder, with a diameter of 35 mm and a height of 335 mm. The volume taken up by the 100 g of powder is measured before any tapping (volume before tapping) and is then measured (volume after tapping) after 2500 taps given from the top to the bottom (drop of 3 mm +/−0.2) using, for example, a Stampf Volumeter STAV 2003 apparatus. This apparatus thus makes it possible to measure, under standardized and reproducible conditions, the compressibility of a powder by calculating the bulk density, the tapped density and, from these data, the compressibility, according to the following formulae:

$$\text{Bulk density}=100 \text{ (g)/volume before tapping (ml)}$$

$$\text{Tapped density}=100 \text{ (g)/volume after tapping (ml)}$$

$$\text{Compressibility (\%)}=[(\text{tapped density}-\text{bulk density})/\text{bulk density}]\times 100$$

The powder according to the invention advantageously has:
a bulk density of between 0.25 and 0.65 g/ml, preferably between 0.30 and 0.60 g/ml, and even more preferentially between 0.35 and 0.55 g/ml,
a tapped density of between 0.40 and 0.80 g/ml, preferably between 0.45 and 0.75 g/ml, and even more preferentially between 0.50 and 0.70 g/ml, and
a compressibility of between 5% and 45%, preferably between 10% and 40%, and even more preferentially between 12% and 35%.

The powder according to the invention advantageously makes it possible to obtain, according to a test D, tablets of 400±10 mg and with a hardness of 100±10 N at a compression force of between 5 and 50 kN, preferably between 8 and 40 kN, even more preferentially between 10 and 25 kN, and even more preferentially between 9 and 25 kN.

The test D consists in measuring the force, expressed in kN, which is required to obtain a tablet with a hardness of 100±10 N prepared using a laboratory reciprocating press of XL1 type, sold by the company Korsch and equipped with flat punches 10 mm in diameter, from said coagglomerate lubricated with 0.5% to 2.0% of magnesium stearate. The lubrication is carried out by mixing the powder and the magnesium stearate for 5 minutes, in an epicyclic mixer of Turbula T2C type (Willy A. Bachofen AG Maschinenfabrik, CH-4005 Basel). The press is adjusted so as to produce tablets of 400 mg'10 mg and with a hardness of 100 N±10 N. The tablet is a cylinder with flat faces, having a diameter of 10 mm. The hardness of the tablets or crushing strength, is measured on a hardness tester of Erweka TBH 30 GMD type, according to the recommendations of the constructor.

The powder according to the invention advantageously allows the preparation of solid forms such as, in particular, tablets or capsules. A subject of the invention is thus also a solid form comprising powder according to the invention and at least one active ingredient. In the present invention, the term "active ingredient" is intended to mean any molecule capable of being introduced into the solid form and of having an application, in particular, in the food, pharmaceutical, nutraceutical, veterinary, phytosanitary, cosmetic, disinfectant and detergent fields. A subject of the invention is therefore also the use of the solid form according to the invention in the abovementioned fields.

The solid form according to the invention advantageously has a property of controlled release of the active ingredient(s) that it contains. Thus, a subject of the present invention is also a solid form characterized in that less than 80%, preferably less than 60%, and even more preferentially less than 40% by weight of the active ingredient thereof is released, according to a test E, after a period of 1 h. The solid form according to the invention is also advantageously characterized in that less than 80%, preferably less than 60%, and even more preferentially less than 50% by weight of the active ingredient thereof is released, according to a test E, after a period of 6 h.

The test E consists in:

mixing 196.0 mg of the powder to be tested with 2.0 mg of magnesium stearate, 2.0 mg of silica (Aerosil 200) and 200.0 mg of active ingredient (anhydrous theophylline with a purity of greater than 99% by weight, sold by the company Sigma) in an epicyclic mixer of Turbula T2C type (Willy A. Bachofen AG Maschinenfabrik, CH-4005 Basel) for 5 minutes, preparing a tablet of 400±10 mg using a reciprocating press of Fette Exacta 21 type equipped with flat punches 10 mm in diameter. The press is adjusted so as to produce tablets of 400±10 mg and with a hardness of 100±10 N. The tablet obtained is a cylinder with flat faces, having a diameter of 10 mm, carrying a dissolution test on the Sotax AT7 smart dissolution control system equipped with a Sotax CY 7-50 piston pump and a Sotax C613 fraction collector. The configuration of the dissolution system is type 2; it is therefore equipped with paddles. The dissolution bath temperature is 37° C. and the paddle speed is 50 revolutions/minute. The first step of the dissolution test consists in immersing the tablet in the dissolution bath containing 500 ml of a saline solution of hydrochloric acid at pH 1.2. During this first step, six samples are taken from the dissolution bath (15; 30; 45; 60; 90; 120 minutes). The second step consists of the addition of 500 ml of phosphate buffer solution ($NaOH+KH_2PO_4$) so as to have 1 l of buffer solution, pH 6.8, said addition of phosphate buffer solution being carried out just after the 120-minute sample is taken. During this second step, twelve samples are taken from the dissolution bath (2.5; 3; 3.5; 4; 5; 6; 7; 8; 9; 10; 11; 12 hours). The theophylline contained in the samples thus taken is, finally, assayed by spectrophotometry at a wavelength of 272 nm.

Finally, a subject of the present invention is the use of the solid forms according to the invention in the food, pharmaceutical, nutraceutical, veterinary, phytosanitary, cosmetic, disinfectant and detergent fields.

The invention will be understood more clearly by means of the examples which follow and of the figures which relate thereto, which aim to be nonlimiting and illustrative and merely refer to certain embodiments and to certain advantageous properties of the powder according to the invention.

EXAMPLE 1

Preparation of Powders According to the Invention 1.1 Powder of Pregelatinized-Starch and of Mannitol A Niro MSD spray-drying tower with a water evaporating capacity of approximately 80 kg/h is used to prepare a powder of cold-soluble pregelatinized starch and of polyol.

An aqueous syrup of mannitol (40% by weight of dry matter, temperature of 80° C.) is sprayed at 40 bar (HP pressure) in the spray-drying chamber using a high-pressure nozzle spraying system (SK 60*21). At the same time, a pulverulent pregelatinized starch (PREGEFLO® CH10 sold by the applicant) is continuously injected, via a weight metering device, at the top of the spray-drying chamber, at a flow rate such that it makes it possible to obtain a mannitol/pregelatinized starch dry/dry weight ratio of 54/46 (M/P ratio).

The spray-drying tower temperatures are adjusted so as to have an upstream air temperature of 135° C. (T° upstream), and a static air bed temperature of 77° C. (T° SFB), thus making it possible to obtain a spray-drying tower outlet air temperature of 63° C. (T° outlet). The fine particles of pregelatinized starch and mannitol (or fines), recovered by cycloning of the outlet air, are re-injected at the head of the spray-drying chamber (top of the spray-drying chamber).

The powder obtained at the outlet of the spray-drying chamber is cooled on the vibrated fluidized bed to a temperature of 20° C. The powder is then sieved on a sieve having a mesh size of 500 µm, the fraction of powder with a particle size of greater than 500 µm being eliminated. A powder of pregelatinized-starch and of mannitol according to the invention is thus collected, which will subsequently be referred to as PREGEL-MAN 1.

1.2 Polysaccharide and Mannitol Powders

The process is carried out as described above, while varying the parameters listed in table 1 and the nature of the cold-soluble polysaccharide as follows:

PREGEL-MAN 1 and 2=waxy corn starch crosslinked with an adipate reagent, mixture of acetic anhydride and of adipic acid, pregelatinized on a drum dryer and sold by the applicant (PREGEFLO® CH10, ROQUETTE FRERES)

PREGEL-MAN 3 and 8=potato starch pregelatinized on a drum dryer and sold by the applicant (PREGEFLO® P100, ROQUETTE FRERES)

PREGEL-MAN 4 and 5=waxy corn starch pregelatinized on a drum dryer and sold by the applicant (PREGEFLO® C100 batch S0960, ROQUETTE FRERES)

PREGEL-MAN 9 and 10=waxy corn starch pregelatinized on a drum dryer and sold by the applicant (PREGEFLO® C100 batch 50988, ROQUETTE FRERES)

PREGEL-MAN 6=corn starch pregelatinized on a drum dryer and sold by the applicant (PREGEFLO® M, ROQUETTE FRERES)

PREGEL-MAN 7=hydroxypropylated pea starch with a degree of substitution (DS) of between 0.16 and 0.21 and pregelatinized on a drum dryer HPMC-MAN 1, 2, 3 and 4=HPMC sold by the company AQUALON (BENECEL® K4M PH CR, IMCD)

CARRA-MAN 1 and 2=carrageenan sold by the company FMC BIOPOLYMER (VISCARIN® GP 209 NF, IMCD)

ALGI-MAN=alginate sold by the company FMC BIOPOLYMER (PROTANAL® LF 120 M, IMCD).

TABLE 1

|  | M/P ratio | Recycling of fines | HP pressure | SK nozzle | T° upstream | T° SFB | T° outlet | Sieving (µm) |
|---|---|---|---|---|---|---|---|---|
| PREGEL-MAN 1 | 54/46 | Top | 40 | 60*21 | 135 | 77 | 63 | 500 |
| PREGEL-MAN 2 | 72/28 | Top | 40 | 60*21 | 150 | 77 | 63 | 500 |
| PREGEL-MAN 3 | 69/31 | Top | 40 | 60*21 | 150 | 77 | 63 | 500 |
| PREGEL-MAN 4 | 54/46 | Top | 40 | 60*21 | 150 | 77 | 63 | 500 |
| PREGEL-MAN 5 | 70/30 | Top | 40 | 60*21 | 150 | 77 | 63 | 500 |
| PREGEL-MAN 6 | 55/45 | Top | 50 | 60*21 | 150 | 77 | 69 | 500 |

TABLE 1-continued

|  | M/P ratio | Recycling of fines | HP pressure | SK nozzle | T° upstream | T° SFB | T° outlet | Sieving (µm) |
|---|---|---|---|---|---|---|---|---|
| PREGEL-MAN 9 | 51/49 | Top | 50 | 60*21 | 150 | 60 | 63 | 500 |
| PREGEL-MAN 10 | 51/49 | Top | 50 | 60*21 | 135 | 65 | 60 | 500 |
| PREGEL-MAN 7 | 56/44 | Top | 40 | 60*21 | 150 | 77 | 62 | 500 |
| PREGEL-MAN 8 | 72/28 | Bottom | 30 | 57*21 | 150 | 65 | 52 | 800 |
| HPMC-MAN 1 | 76/24 | Bottom | 30 | 57*21 | 160 | 65 | 59 | 800 |
| HPMC-MAN 2 | 83/17 | Bottom | 30 | 57*21 | 150 | 65 | 52 | 800 |
| HPMC-MAN 3 | 49/51 | Bottom | 40 | 60*21 | 150 | 65 | 54 | 800 |
| HPMC-MAN 4 | 62/38 | Top | 50 | 60*21 | 160 | 60 | 65 | 500 |
| CARRA-MAN 1 | 83/17 | Bottom | 30 | 57*21 | 150 | 65 | 52 | 800 |
| CARRA-MAN 2 | 78/22 | Bottom | 30 | 57*21 | 150 | 65 | 52 | 800 |
| ALGI-MAN | 85/15 | Bottom | 30 | 57*21 | 150 | 65 | 52 | 800 |

EXAMPLE 2

Characteristics of the Powders According to the Invention and Comparisons

The powders according to the invention described in the previous example (table 1) were characterized in terms of:

flow time, measured in seconds and evaluated according to the test B, bulk and tapped densities, measured in g/ml and evaluated according to the test C, compressibility, evaluated as % according to the test C, viscosity, measured in Pa/s and evaluated according to the test A, volume mean diameter D4,3, measured in pm and determined on an LS 13-320 LASER diffraction particle size analyzer from the company Beckman-Coulter as previously described.

The characteristics of the powders according to the invention are also compared (Table 2) with those of the polysaccharides taken in isolation:

PREGEL=waxy corn starch crosslinked with an adipate reagent, mixture of acetic anhydride and of adipic acid, pregelatinized on a drum dryer and sold by the applicant (PREGEFLO® CH10, ROQUETTE FRERES)

HPMC=HPMC sold by the company AQUALON (BENECEL® K4M PH CR, IMCD)

CARRA=carrageenan sold by the company FMC BIOPOLYMER (VISCARIN® GP 209 NF, IMCD)

ALGI=alginate sold by the company FMC BIOPOLYMER (PROTANAL® LF 120 M, IMCD)

and with those of simple physical mixtures of polysaccharides/mannitol:

PREGEL+MAN=physical mixture (M/P ratio by weight 50/50) of mannitol (PEARLITOL® 160C, ROQUETTE FRERES) and waxy corn starch crosslinked with an adipate reagent, mixture of acetic anhydride and adipic acid, pregelatinized on a drum dryer and sold by the applicant (PREGEFLO® CH10, ROQUETTE FRERES)

HPMC+MAN=physical mixture (M/P ratio by weight 83/17) of mannitol (PEARLITOL® 160C, ROQUETTE FRERES) and HPMC sold by the company AQUALON (BENECEL® K4M PH CR, IMCD).

TABLE 2

|  | Flow time (s) | Bulk density (g/ml) | Tapped density (g/ml) | Compressibility (%) | Viscosity (Pa·s⁻¹) | D4,3 (µm) |
|---|---|---|---|---|---|---|
| PREGEL | ∞ | 0.490 | 0.676 | 38.0 | 35.0 | 39.3 |
| PREGEL + MAN | ∞ | 0.532 | 0.725 | 36.3 | 3.3 | 58.2 |
| PREGEL-MAN 1 | 6 | 0.477 | 0.544 | 14.0 | 0.8 | 157.1 |
| PREGEL-MAN 2 | 7 | 0.529 | 0.599 | 12.0 | 0.6 | 138.6 |
| PREGEL-MAN 3 | 8 | 0.523 | 0.605 | 15.7 | 0.4 | 160.3 |
| PREGEL-MAN 4 | 8 | 0.467 | 0.557 | 19.3 | 1.7 | 136.6 |
| PREGEL-MAN 5 | 8 | 0.523 | 0.603 | 13.0 | 0.5 | 162.5 |
| PREGEL-MAN 6 | 5 | 0.501 | 0.602 | 20.2 | 0.8 | 154.8 |
| PREGEL-MAN 9 | 7 | 0.427 | 0.543 | 21.4 | 0.5 | 118.0 |
| PREGEL-MAN 10 | 7 | 0.435 | 0.529 | 17.8 | 0.6 | 145.0 |
| PREGEL-MAN 7 | 5 | 0.452 | 0.608 | 34.5 | 0.6 | 143.1 |
| PREGEL-MAN 8 | 7 | 0.439 | 0.542 | 23.5 | 0.4 | 242.9 |
| HPMC | ∞ | 0.321 | 0.510 | 58.9 | 518.0 | 135.4 |
| HPMC + MAN | ∞ | 0.505 | 0.758 | 50.1 | 1.7 | 98.9 |
| HPMC-MAN 1 | 8 | 0.357 | 0.510 | 42.9 | 6.9 | 223.7 |
| HPMC-MAN 2 | 12 | 0.316 | 0.410 | 29.7 | 3.2 | 277.9 |
| HPMC-MAN 3 | 10 | 0.321 | 0.433 | 35.0 | 75.1 | 299.8 |
| HPMC-MAN 4 | 10 | 0.337 | 0.418 | 19.4 | 52.2 | 165.0 |
| CARRA | ∞ | nf | nf | nf | 368.0 | 69.4 |
| CARRA-MAN 1 | 7 | 0.413 | 0.515 | 24.7 | 3.3 | 235.2 |
| CARRA-MAN 2 | 7 | 0.42 | 0.526 | 25.2 | 6.9 | 206.4 |
| ALGI | ∞ | nf | nf | nf | 329.0 | 52.0 |
| ALGI-MAN | 6 | 0.431 | 0.541 | 25.5 | 0.5 | 272.7 |

∞ = infinite time; nf = not found.

Compared with the polysaccharides taken in isolation or with the simple physical mixtures, the powders according to the invention exhibit an excellent flow (flow time less than 15 seconds), a lower viscosity and a higher volume mean diameter D4,3.

EXAMPLE 3

Evaluation of the Compressibility of the Powders According to the Invention and Comparisons The powders according to the invention which are described in example 1 (table 1), some polysaccharides taken in isolation, and simple physical mixtures of polysaccharide/mannitol were characterized in terms of compressibility according to the test D (table 3).

TABLE 3

|  | Magnesium stearate content (%) | Compression force (kN) |
|---|---|---|
| PREGEL | 0.5 | x |
| PREGEL + MAN | 0.5 | 18.7 |

TABLE 3-continued

|  | Magnesium stearate content (%) | Compression force (kN) |
| --- | --- | --- |
| PREGEL-MAN 1 | 1.0 | 23.6 |
| PREGEL-MAN 2 | 1.0 | 12.1 |
| PREGEL-MAN 3 | 1.0 | 12.0 |
| PREGEL-MAN 4 | 1.0 | 15.1 |
| PREGEL-MAN 5 | 1.0 | 14.3 |
| PREGEL-MAN 6 | 1.0 | 20.0 |
| PREGEL-MAN 9 | 0.5 | 10.0 |
| PREGEL-MAN 10 | 0.5 | 14.0 |
| PREGEL-MAN 7 | 1.0 | 21.5 |
| PREGEL-MAN 8 | 1.0 | 19.9 |
| HPMC | 2.0 | x |
| HPMC + MAN | 2.0 | x |
| HPMC-MAN 1 | 0.5 | 11.8 |
| HPMC-MAN 2 | 1.0 | 10.5 |
| HPMC-MAN 3 | 1.0 | 10.3 |
| HPMC-MAN 4 | 0.5 | 9.3 |
| CARRA-MAN 1 | 0.5 | 11.2 |
| CARRA-MAN 2 | 2.0 | 11.3 |
| ALGI-MAN | 0.5 | 11.6 | x = impossible to prepare tablets of the required hardness regardless of the compression force applied.

Contrary to the polysaccharides taken in isolation and to certain polysaccharide/mannitol physical mixtures, the powders according to the invention make it possible to obtain, according to a test D, tablets with a hardness of 100±10 N at a compression force of less than 25 kN.

EXAMPLE 4

Dissolution Profile of the Solid Forms According to the Invention and Comparisons The properties of controlled release of an active ingredient (theophylline) of the solid forms according to the invention, and of solid forms obtained from certain polysaccharides taken in isolation and from simple physical mixtures of polysaccharide/mannitol, were evaluated according to the test E (FIG. 1).

The solid forms according to the invention exhibit a theophylline controlled release of less than 80% by weight of theophylline after a period of 1 h. Moreover, certain solid forms according to the invention also advantageously exhibit a theophylline controlled release of less than 60% by weight of theophylline after a period of 6 h.

EXAMPLE 5

Scanning Microscopy Observations of Powders According to the Invention

The powders according to the invention were observed by scanning electromicroscopy, ESEM-FEI-Quanta FEG 200. FIGS. 2 to 5 are the result of photographs of these observations.

FIG. 2: PREGEL-MAN 4 (magnification: 136 times)
FIG. 3: PREGEL-MAN 4 (magnification: 340 times)
FIG. 4: PREGEL-MAN 1 (magnification: 680 times)
FIG. 5: PREGEL-MAN 5 (magnification: 680 times)

The invention claimed is:

1. A powder of cold-soluble-polysaccharide and of polyol, obtained by agglomeration of said polysaccharide in dry and particulate form with said polyol, said agglomeration resulting from the drying or dehydration of a syrup of said polyol sprayed onto or around the polysaccharide in particulate form, particles of the powder having an irregular, non-spherical shape, in which the cold-soluble-polysaccharide is in the particulate form and is clearly visible at the surface of said particles and in which the polyol is predominantly in crystalline form.

2. The powder of claim 1, wherein the polyol/polysaccharide ratio is between 95/5 and 30/70.

3. The powder of claim 1, wherein the polyol is selected from the group consisting of mannitol, sorbitol, isomalt, and mixtures thereof.

4. The powder of claim 1, wherein the polysaccharide is selected from the group consisting of hydroxyethylcellulose (HEC), hydroxypropylcellulose (HPC) or hydroxypropylmethylcellulose (HPMC), native or chemically modified pregelatinized starches, agar-agar, carrageenans, alginates and salts thereof, xanthan gum, pullulan, and mixtures thereof.

5. The powder of claim 1, wherein said powder has a particle size D4, 3 of between 50 and 500 μm.

6. The powder of claim 1, wherein said powder has a viscosity in water, evaluated according to a test A, of between 100 mPa.s$^{-1}$ and 10,000 Pa.s$^{-1}$.

7. The powder of claim 1, wherein said powder has a flow time, determined according to a test B, of between 3 and 15 seconds.

8. The powder of claim 1, wherein said powder has a compressibility, determined according to a test C, of between 5% and 45%.

9. The powder of claim 1, wherein said powder makes it possible to obtain, according to a test D, tablets with a hardness of 100±10 N at a compression force of between 5 and 50 kN.

10. A method for preparing a powder according to claim 1, comprising a texturing step comprising spraying a polyol syrup onto a cold-soluble polysaccharide in particulate form, and simultaneously drying said polyol syrup.

11. The method of claim 10, wherein the texturing step also comprises recycling of a powder fraction.

12. The method of claim 10, wherein the texturing step is carried out in a spray-drying tower.

13. The method of claim 10, wherein the texturing step is carried out in a fluidized air bed granulator.

14. A solid form comprising powder according to claim 1, and at least one active ingredient.

15. The solid form of claim 14, wherein less than 80%, by weight of the active ingredient is released, according to a test E, after a period of 1 h.

16. The solid form of claim 14, wherein less than 80%, by weight of the active ingredient is released, according to a test E, after a period of 6 h.

17. The solid form of claim 15, wherein less than 80%, by weight of the active ingredient is released, according to a test E, after a period of 6 h.

* * * * *